United States Patent
Simmons (10) Patent No.: US 7,052,421 B2
(45) Date of Patent: May 30, 2006

(54) BELT TENSIONING SYSTEM FOR USE WITH A MOTORIZED MOBILE C-ARM

(75) Inventor: John M. Simmons, West Jordan, UT (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 400 days.

(21) Appl. No.: 10/611,006

(22) Filed: Jul. 1, 2003

(65) Prior Publication Data

US 2005/0003914 A1    Jan. 6, 2005

(51) Int. Cl.
*F16H 7/08* (2006.01)
*H05G 1/02* (2006.01)

(52) U.S. Cl. ............... 474/101; 474/115; 474/117; 378/197

(58) Field of Classification Search ........ 474/101, 474/109, 112–115, 117, 133, 135–138; 378/167, 378/189, 195–198, 181, 15, 17, 49; 417/53, 417/362
See application file for complete search history.

(56) References Cited

U.S. PATENT DOCUMENTS

| | | | |
|---|---|---|---|
| 3,281,598 A | | 10/1966 | Hollstein |
| 3,477,670 A | | 11/1969 | Sloyan |
| 4,358,856 A | * | 11/1982 | Stivender et al. ........... 378/167 |
| 5,046,495 A | | 9/1991 | Takahashi et al. |
| 5,295,918 A | * | 3/1994 | Campbell et al. ........... 474/101 |
| 5,982,844 A | | 11/1999 | Tybinkowski et al. |
| 6,004,112 A | * | 12/1999 | Cook et al. ................. 417/362 |
| 6,030,305 A | * | 2/2000 | Hood .......................... 474/109 |
| 6,180,943 B1 | | 1/2001 | Lange |
| 6,452,998 B1 | * | 9/2002 | Tybinkowski et al. ........ 378/17 |
| 6,789,941 B1 | * | 9/2004 | Grady ......................... 378/197 |

* cited by examiner

*Primary Examiner*—Marcus Charles
(74) *Attorney, Agent, or Firm*—McAndrews, Held & Malloy, Ltd.; Peter J. Vogel; Michael A. Dellapenna (57) ABSTRACT

A drive system for an imaging device of the type having a curved arm. The drive system includes a carrier that engages and supports the curved arm such that the curved arm can be moved along the carrier. The drive system includes a belt extending through the carrier and secured about the periphery of the curved arm. The drive system receives and drives the belt to move the curved arm relative to the carrier. The drive system includes a tensioning mechanism configured to move in such a direction relative to the carrier in order to increase the tension on the belt and to move in such a direction relative to the carrier in order to decrease the tension on the belt.

20 Claims, 6 Drawing Sheets

BELT TENSIONING SYSTEM FOR USE WITH A MOTORIZED MOBILE C-ARM

BACKGROUND OF THE INVENTION

The present invention relates to a system for tensioning a belt. More particularly, certain embodiments of the present invention relate to a pivot plate that engages a belt on a mobile C-arm to increase the tension of the belt.

Before and during a medical procedure, medical professionals may need to take several different images of a patient's body from a number of different orientations. Often it is difficult to effectively capture images from certain orientations where the imaging device is fixed and stationary. Therefore, imaging devices are mounted on large, mobile structures known as C-arm imaging machines. C-arm imaging machines typically include a mobile support structure, a carrier, and a curved, C-shaped positioning arm, (or C-arm). The carrier is mounted on the support structure and the C-arm is, in turn, slidably mounted to the carrier. An imaging source is located on one distal end of the C-arm and an imaging receiver is located on the other distal end of the C-arm. The C-arm imaging machine may be moved and rotated about a patient in a number of different orientations such that the patient is positioned between the imaging source and the imaging receiver. The C-arm imaging machine operator may then take an image of the patient.

The C-arm typically may be rotated about the patient in at least two ways. The support structure includes a rotation arm that is connected to the carrier. The C-arm has tracks along an outer periphery thereof that capture rollers on the carrier such that the C-arm is movably retained to the carrier along the rollers. A large belt extends from the carrier around the arms of the C-arm. The rotation arm may be rotated about a rotational axis such that the C-arm also rotates about the rotational axis. This is known as the rotational rotation of the C-arm. Additionally, the C-arm may be rotated along the plane of the C-arm about a transverse axis by moving the belt such that the C-arm moves, or rotates, along the carrier. This is known as orbital rotation of the C-arm. By being rotatable about at least two different axes, the C-arm may be positioned at many different orientations about a patient in order to take images from different desirable perspectives. Thus, the mobile C-arm imaging machine greatly increases the efficiency and ease of taking images of a patient before and during a medical procedure.

However, the conventional mobile C-arm imaging machine has a number of drawbacks. First, many C-arms may only be moved manually for either orbital or rotational rotation. That is to say, an operator must manually release a brake and then manipulate the C-arm to move the C-arm to a desired position. The operator then manually stops the movement of the C-arm when it reaches its desired position and activates the brake to lock the C-arm in place. This method of adjusting the position of the C-arm can be difficult and time-consuming, especially if the person performing the medical procedure must also manipulate the C-arm. Additionally, this method of adjusting the position of the C-arm may lead to imprecise positioning by the operator or any other number of problems caused by human error.

Some conventional C-arms have a drive train that is connected to the C-arm such that an operator can use the drive train to mechanically drive the C-arm to orbitally rotate about the carrier. The operator can thus control the movement of the C-arm by operating a joystick that is electrically connected to the drive train. However, often the C-arm imaging machines that incorporate such drive trains are large fixed-room devices that cannot be moved out of a room for use. Additionally, the drive train is in a fixed position such that is cannot be moved with the C-arm and thus may take up space and get in the way of operation of the C-arm. Additionally, there are other conventional C-arms that are mobile and incorporate a drive train, but these C-arms do not use a belt to drive the C-arm.

Another problem associated with conventional C-arm imaging machines is maintaining tension in the belt as it engages the C-arm, and, if applicable, the drive train. The belt needs to be tensioned about the C-arm and the carrier in order that an operator can effectively move the belt and thus cause the C-arm to rotate orbitally. If the belt is not adequately tensioned, the belt may be delayed in engaging the distal ends of the C-arm. Also, in C-arms that include drive trains, if the belt is not adequately tensioned, the drive train may not fully engage the belt or the belt may lay even loosely about the rotating pulleys of the drive train.

Thus, many conventional C-arms include a tensioning system, or spring, located at a first distal end of the C-arm that resistibly engages the belt and pushes the belt away from the C-arm in order to tension the belt about the C-arm. The C-arms do not necessarily include a spring at the opposite second distal end of the C-arm. Because the spring is located at only the first end of the C-arm, the tension in the belt decreases at points further away from the first end. If the C-arm includes a drive train, the drive train engages the belt between the two distal ends of the C-arm. Therefore, the tension of the belt is different on either side of where the belt is connected to the drive train. For example, the section of the belt extending from the drive train to the second distal end is not as tensioned as the section of the belt extending from the drive train to the first distal end. Because of the increased slack in the belt between the second distal end and the drive train, rotation of the C-arm may be delayed where the operator tries to rotate the second distal end toward the drive train.

Additionally, locating the tensioning system at either end or both ends of the C-arm takes up space such that the tensioning system may limit the mobility of the C-arm or get in the way of the operator or medical procedure taking place.

Therefore, a need exists for an improved tensioning and drive system for a belt used to move a C-arm.

BRIEF SUMMARY OF THE INVENTION

Certain embodiments of the present invention include a drive system for an imaging device of the type having a curved arm. The drive system includes a carrier that engages and supports the curved arm such that the curved arm can be moved along the carrier. The drive system includes a belt extending through the carrier and secured about the periphery of the curved arm. The drive system receives and drives the belt to move the curved arm relative to the carrier. The drive system includes a tensioning mechanism configured to move in such a direction relative to the carrier in order to increase the tension on the belt and to move in such a direction relative to the carrier in order to decrease the tension on the belt.

Certain embodiments of the present invention include a drive system. The drive system includes a mobile curved arm and a carrier that engages the curved arm. The carrier includes a spring mechanism connected thereto. The drive system includes a belt that extends through the carrier and is secured about the periphery of the curved arm. The drive system is configured to pivot about the carrier. The drive system receives and drives the belt such that the curved arm moves relative to the carrier. The drive system is configured to receive an engagement piece such that the engagement piece engages the spring mechanism. The spring mechanism resists the engagement piece such that the drive system is pivoted in such a direction relative to the carrier that the drive system is pulled away from the curved arm and the belt increases in tension about the curved arm.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentality shown in the attached drawings.

DETAILED DESCRIPTION OF THE INVENTION

Figure 1:
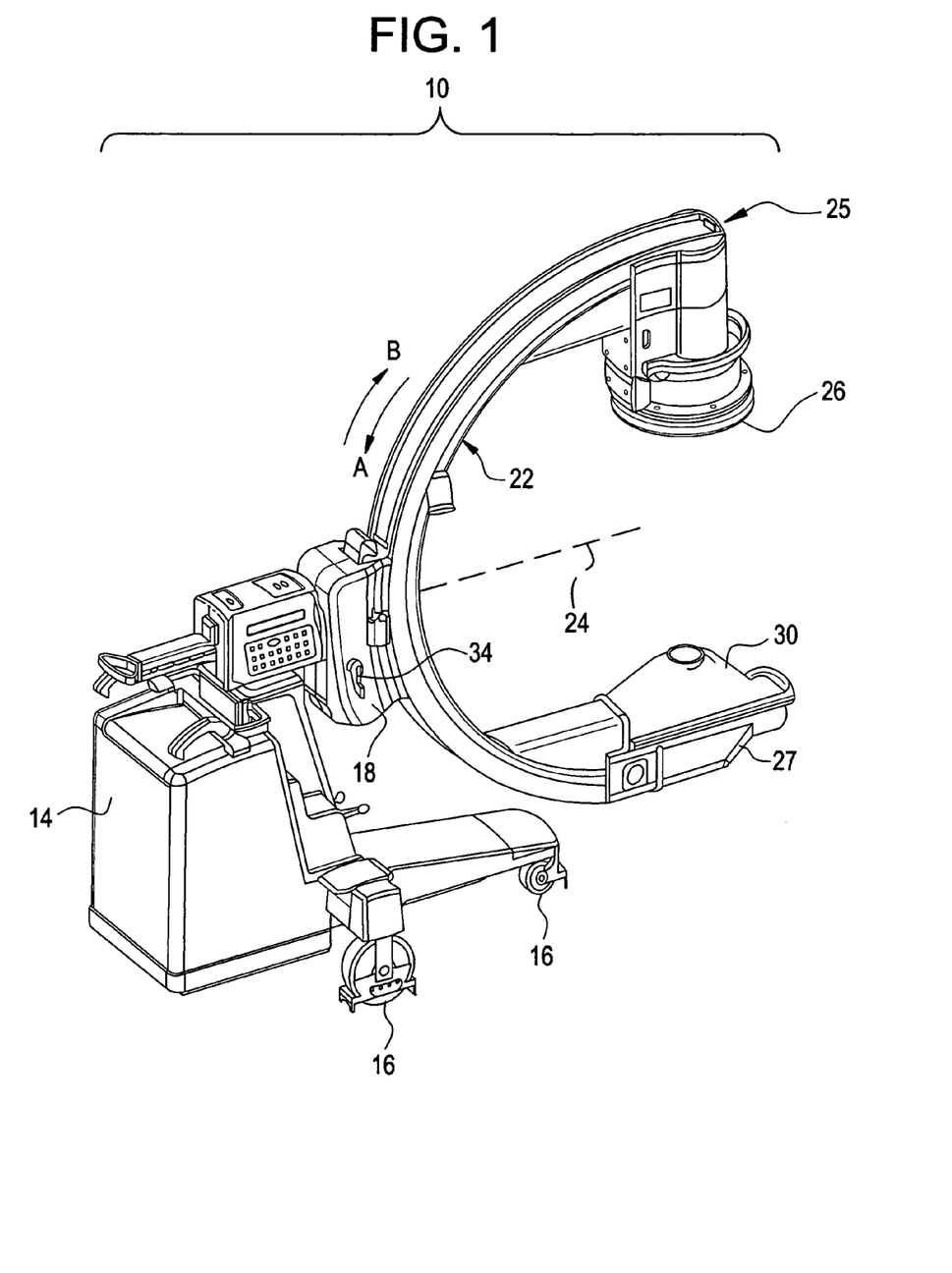
FIG. 1 is an isometric side view of a mobile imaging machine formed according to an embodiment of the present invention.

FIG. 1 is an isometric side view of a mobile imaging machine 10 formed according to an embodiment of the present invention. The imaging machine 10 includes a mobile support structure 14, a carrier 18 and a curved positioning arm 22 (which is illustrated as a C-arm). Although the curved arm 22 is illustrated as a C-arm, it will be appreciated the arm 22 may have different shapes. For example, the arm 22 may be spiral in shape. The mobile support structure 14 has wheels 16, which allow the entire imaging machine 10 to be moved. The C-arm 22 is semicircular in shape and carries an imaging receiver 26 at a first distal end 25 and an imaging source 30 at a second distal end 27. By way of example and not limitation, the imaging source 30 may be an x-ray source. Alternatively, the C-arm 22 may have different shapes, for example, the C-arm 22 may be spiral in shape. A partially covered drive train 34 is mounted to the carrier 18.

Figure 3:
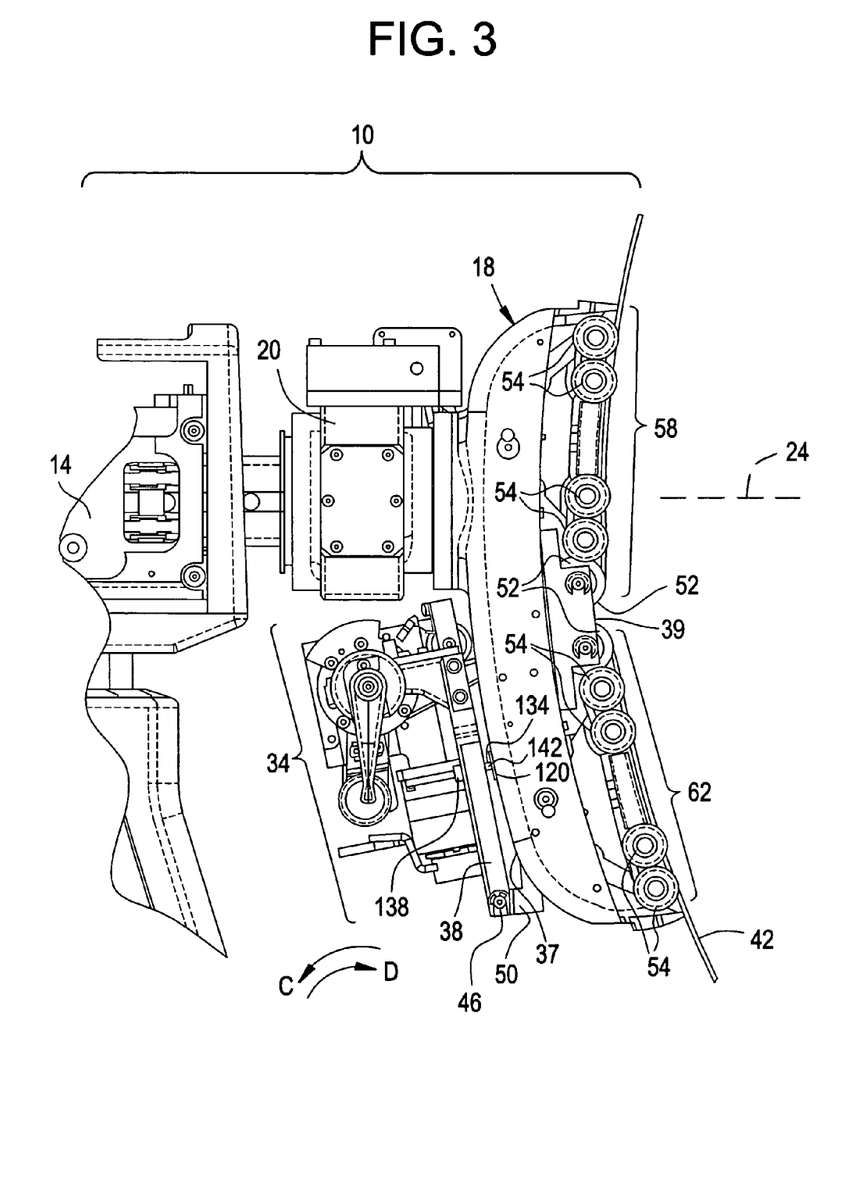
FIG. 3 is a side view of the imaging machine of FIG. 1 with a drive train exposed and the C-arm removed.

FIG. 3 is a partial side view of the imaging machine 10 of FIG. 1 with the drive train 34 exposed and the C-arm 22 (FIG. 1) removed. The mobile support structure 14 includes a rotational knuckle 20 that extends to the carrier 18. The rotational knuckle 20 may be manually rotated about a longitudinal axis 24 such that the entire C-arm 22 is rotated about the longitudinal axis 24. Alternatively, the rotational knuckle 20 may be driven by a motor, such as an electric motor (not shown). The motor in turn is electrically connected to a controlling device (not shown) such as a joystick to allow the operator to control the movement of the rotational knuckle 20 with the joystick.

Figure 2:
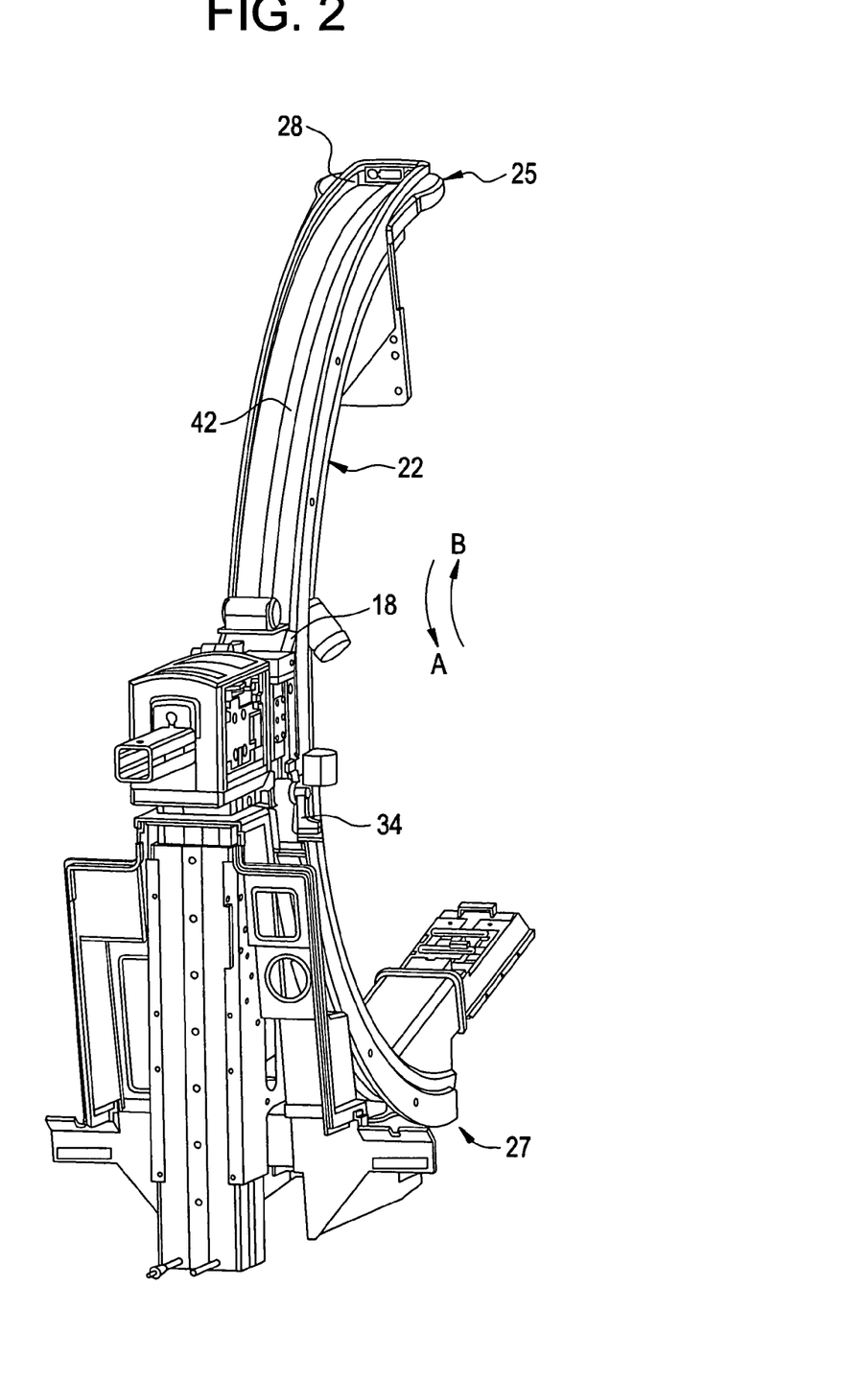
FIG. 2 is a rear isometric side view of the mobile imaging machine of FIG. 1.

FIG. 2 is a rear isometric view of the mobile imaging machine 10 of FIG. 1. The C-arm 22 is movably mounted to the carrier 18. A belt 42 extends from the drive train 34 through the carrier 18, about the outer periphery of the C-arm 22 and is connected to the C-arm 22 at each distal end 25 and 27. Alternatively, the belt 42 may extend about the inner periphery of the C-arm 22. Alternatively, the belt 42 may be connected to the C-arm 22 at any number of different points besides the distal ends 25 and 27.

Returning to FIG. 1, an operator may activate the drive train 34 by pressing a button or switch connected to the drive train 34 such that the drive train 34 engages the belt 42 (FIG. 2) in order to orbitally rotate the C-arm 22 along the carrier 18 in the direction of either arrow A or B. Alternatively, the drive train 34 may be electrically connected to an electronic controlling device (not shown) such as a joystick in order that the operator can control the movement of the C-arm 22 with the joystick.

In operation, an operator may roll the mobile imaging machine 10 proximate a patient that is to be imaged. The operator may rotate the C-arm 22 about the longitudinal axis 24 of the rotational knuckle 20 (FIG. 3) to position the C-arm 22 about the patient. The operator may also activate the drive train 34 in order to orbitally rotate the C-arm 22 along the carrier 18 and about the patient in the direction of either arrow A or B. The operator orbitally rotates the C-arm 22 along the belt 42 (FIG. 2) in order to position the C-arm 22 about the patient such that the patient is situated between the imaging source 30 and imaging receiver 26. The operator may take an image (or series of images) of the patient and then move the C-arm 22 away from the patient.

Returning to FIG. 3, the drive train 34 is mounted on a flat, substrate-shaped plate 38. Alternatively, the plate 38 may have any number of different shapes or thicknesses. The plate 38 is connected to a foot 50 extending from a backside 37 of the carrier 18 by a pin 46 such that the plate 38 can rotate about the pin 46 in the directions of arrows C and D. The belt 42 extends from the drive train 34 through the plate 38 to the carrier 18. The belt 42 extends through a hole (not shown) located midway along the carrier 18 from the backside 37 of the carrier 18 to an inner side 39 of the carrier 18 to engage the C-arm 22 (FIG. 1). The carrier 18 has an upper portion 58 on one side of the hole and a lower portion 62 on the other side of the hole. The upper and lower portions 58 and 62 each have an idler wheel 52 proximate the hole. The belt 42 extends about the idler wheels 52, and the idler wheels 52 direct the belt 42 along the carrier 18. The idler wheels 52 do not engage the C-arm 22. The upper and lower portions 58 and 62 also each have sets of rollers 54 located on the inner side 39 of the carrier 18. The belt 42 extends through the hole such that a first portion of the belt 42 extends along the upper portion 58 and a second portion of the belt 42 extends along the lower portion 62.

Returning to FIG. 2, the C-arm 22 has tracks 28 extending along the outer periphery thereof that capture the rollers 54 (FIG. 3) in order to retain the C-arm 22 to the carrier 18. In operation, when the C-arm 22 is connected to the belt 42 and the rollers 54, the drive train 34 activates the belt 42 such that the belt 42 can pull the C-arm 22 along the rollers 54 in the direction of either arrow A or B.

Figure 6:
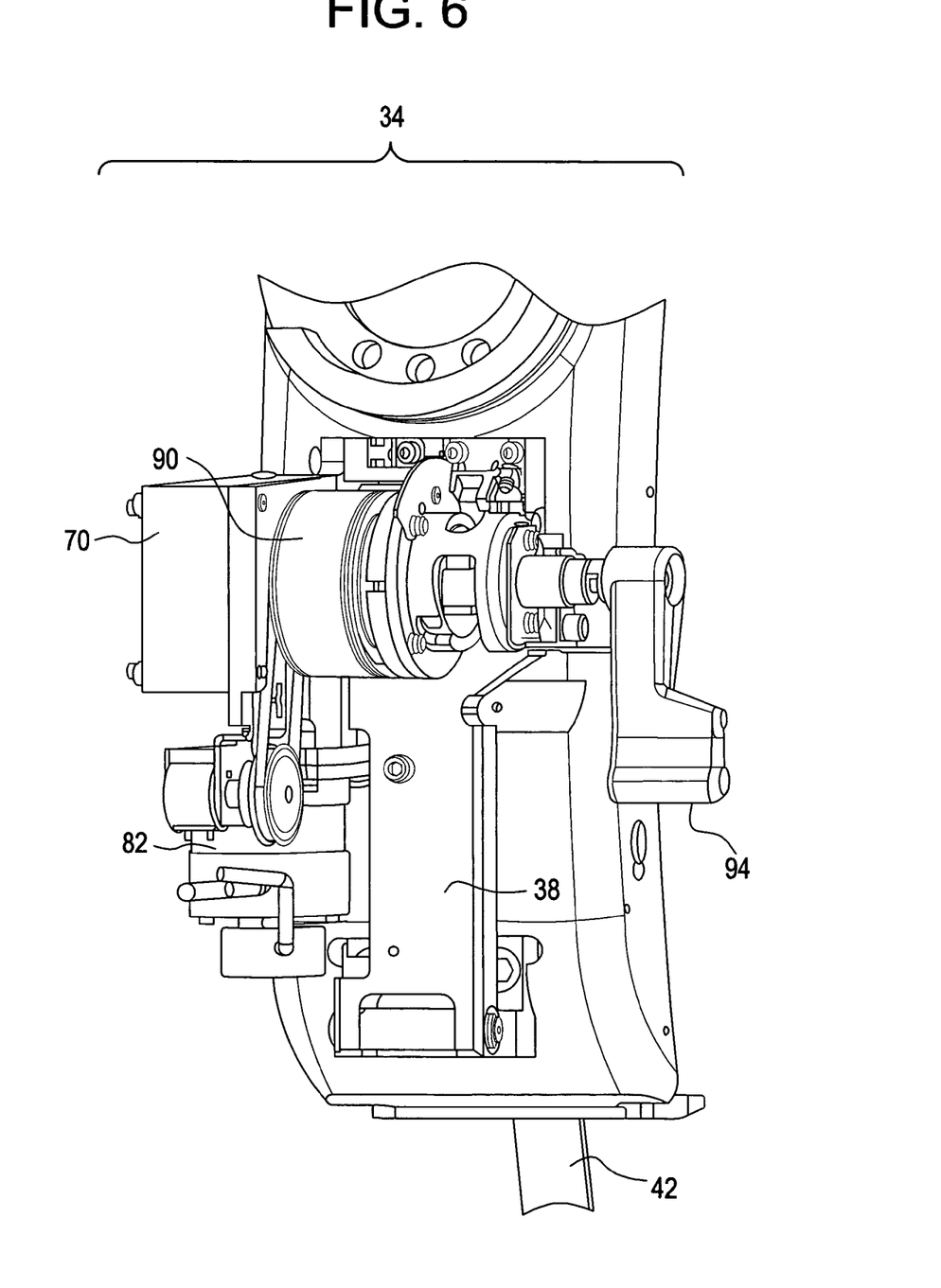
FIG. 6 is a rear isometric view of the drive train of FIG. 2.

FIG. 6 is a rear isometric view of the drive train 34 of FIG. 2. The drive train 34 includes a motor 82 connected to a drive shaft 86 (FIG. 4) through a gear box 70. The gear box 70 is mounted to the plate 38. The drive shaft 86 is connected to a drive pulley 90. The drive pulley 90 drives the belt 42 to effect orbital rotation of the C-arm 22 (FIG. 1) as explained below. A clutch release handle 94 can be rotated to disengage the drive pulley 90 from a drive shaft 86 to allow manual manipulation of the C-arm 22.

Figure 4:
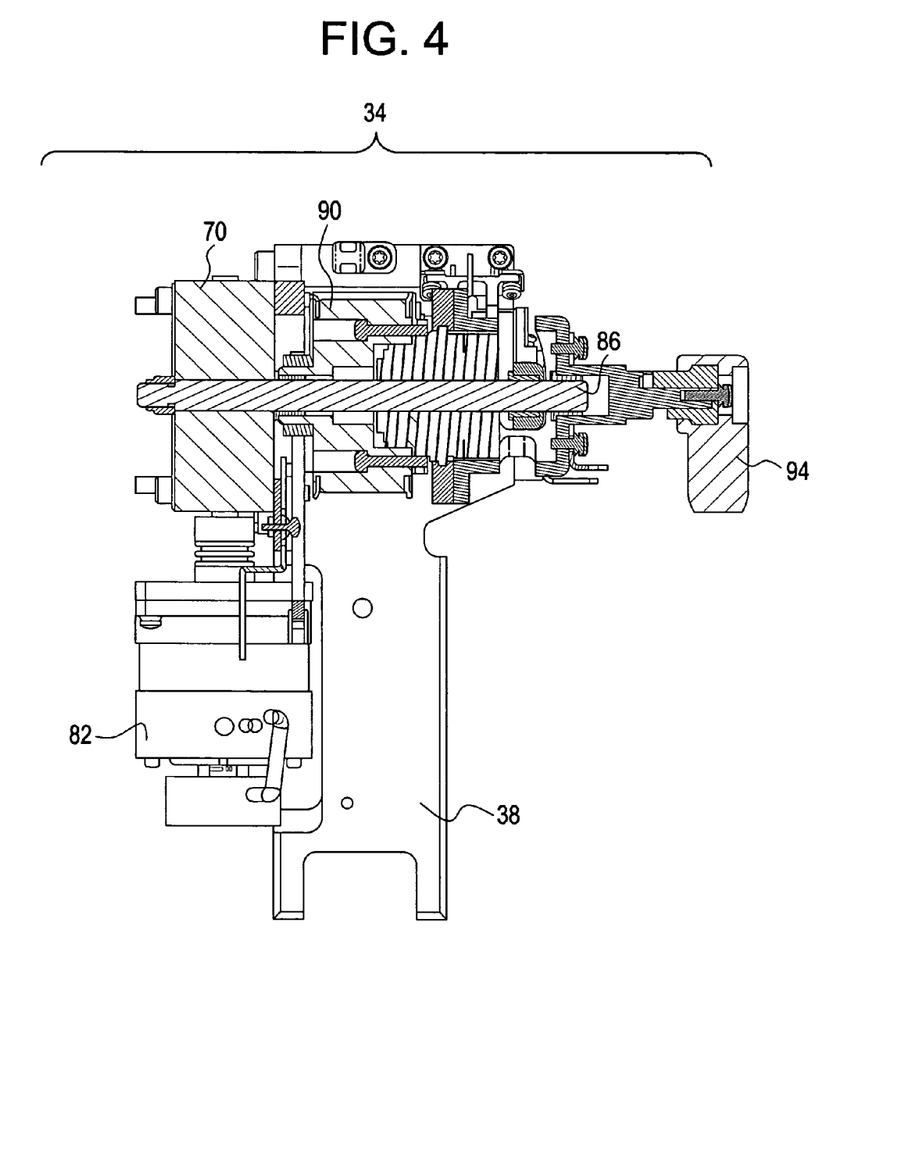
FIG. 4 is a top cutaway view of a drive train formed according to an embodiment of the present invention.

FIG. 4 is a top cutaway view of the drive train 34 formed according to an embodiment of the present invention. A drive shaft 86 extends from the gear box 70 to the clutch release handle 94. The motor 82 is configured to drive the drive shaft 86. The drive shaft 86 engages gears within the gear box 70. The drive shaft 86 is not back-drivable, which is to say that the drive shaft 86 cannot be turned to engage the gears within the gear box 70 or the motor 82. The cylindrical drive pulley 90 is mounted to the drive shaft 86. The belt 42 (FIG. 2) is wrapped around the drive pulley 90 and extends through the plate 38 to the carrier 18 (FIG. 2). The drive pulley 90 and the belt 42 both have teeth (not shown) that engage each other in order that the belt 42 engages and moves along with the drive pulley 90 when the drive pulley 90 rotates instead of remaining stationary as the drive pulley 90 rotates.

In operation, the motor 82 is activated remotely by a joystick as described above such that the motor 82 causes the drive shaft 86 to rotate. As the drive shaft 86 rotates, the drive pulley 90 is rotated with it. The rotating drive pulley 90 causes the belt 42 (FIG. 3) to move in the direction of the rotation of the drive pulley 90. Thus, as the belt 42 moves across the drive pulley 90 through the drive train 34, one of the distal ends 25 or 27 of the C-arm 22 (FIG. 1) is pulled toward the carrier 18 (FIG. 1) such that the C-arm 22 rotates. The drive train 34 is configured such that the drive shaft 86 may be rotated either clockwise or counter-clockwise to effect the movement of either distal end 25 or 27 of the C-arm 22 toward the carrier 18. Additionally, an operator can rotate the clutch release handle 94 in order to disengage the drive pulley 90 from the drive shaft 86 and thus manipulate the C-arm 22 manually instead of by the drive train 34.

Figure 5:
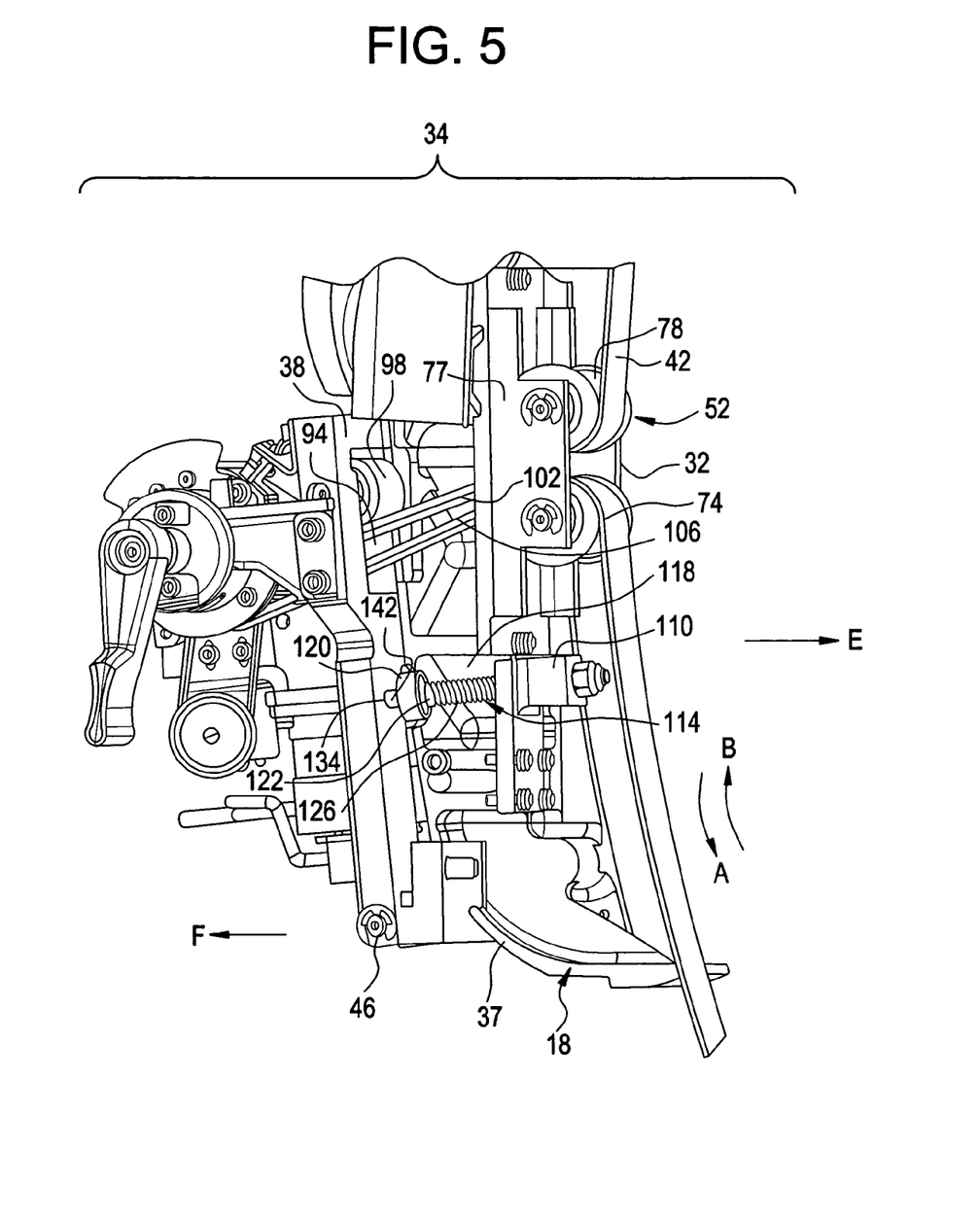
FIG. 5 is an isometric view of a drive train and a cutaway isometric view of a C-arm carrier formed according to an embodiment of the present invention.

FIG. 5 is an isometric view of the drive train 34 and a cutaway isometric view of the carrier 18 formed according to an embodiment of the present invention. As shown, the belt 42 is wrapped around the drive pulley 90 (FIG. 6) and extends through a hole 94 in the plate 38 to the carrier 18. The drive train 34 includes an additional pulley 98 in the hole 94 that engages a first portion 102 of the belt 42 extending from a first side of the drive pulley 90 through the hole 94. The pulley engages the first portion 102 of the belt 42 such that the first portion 102 is redirected in order to be generally aligned with a second portion 106 of the belt 42 extending from a second side of the drive pulley 90 through the hole 94. Thus, the pulley 98 tightens the belt 42 around the drive pulley 90 and aligns the first and second portions 102 and 106 of the belt 42 as the belt 42 is fed through the hole in the carrier 18 to the rollers 54 (FIG. 3).

As shown, the idler wheels 52 are mounted along the inner side 32 of the carrier 18 on a frame 77. Each idler wheel 52 has rims 74 positioned at opposite ends of a cylinder 78. The rims 74 have a first diameter and the cylinder 78 has a second diameter, with the first diameter being greater than the second diameter. Thus, the belt 42 extending through the carrier 18 is positioned between the rims 74 and along the cylinder 78 of each idler wheel 52 to guide the belt 42 to the rollers 54 (FIG. 3). As described above in regard to FIG. 4, the drive train 34 operates to move the belt 42, and thus the C-arm 22 in the direction of arrow A or B, depending on the preference of the operator.

The drive train 34 is held in position about the backside 37 of the carrier 18 by the pin 46 and by the belt 42 which is wrapped around the drive pulley 90 (FIG. 4). As can be seen in FIG. 5, the carrier 18 includes an L-shaped spring block 110 that is screwed therein. A spring plunger 114 is fastened into the spring block 110 and extends through a gap 118 in the carrier 18 to a position proximate the plate 38. The spring plunger 114 includes a cylindrical shaft 122 and a spring 126 disposed about the shaft 122. One end of the shaft 122 is slidably mounted in the spring block 110 such that the shaft 122 may be slid into and out of the spring block 110. A cap 120 is connected to the other end of the spring plunger 114. The spring 126 is positioned on the shaft 122 between the spring block 110 and the cap 120 such that the spring 126 pushes against the cap 120. The plate 38 carries a screw 134 that is threaded through a hole in the plate 38 and is aligned to engage the cap 120.

Returning to FIG. 3, the screw 134 is shown extending through the plate 38. A first portion 138 of the screw 134 extends from a first side of the plate 38 and a second portion 142 of the screw 134 extends from a second side of the plate 38. In operation, an operator may engage the first portion 138 of the screw 134 by hand or with a tool to screw the screw 134 further into the plate 38 such that the second portion 142 of the screw 134 extends further out the opposite side of the plate 38. As the second portion 142 of the screw 134 extends further out of the plate 38, the second portion 142 engages the cap 120.

Returning to FIG. 5, the second portion 142 of the screw 134 pushes the cap 120 in the direction of arrow E. As the cap 120 is pushed in the direction of arrow E, the cap 120 pushes the shaft 122 further into the spring block 110. The spring 126 is compressed between the cap 120 and the spring block 110 and resistibly engages the cap 120 in order to limit the distance the cap 120 and the shaft 122 travel in the direction of arrow E. As the second portion 142 of the screw 134 engages resistance from the spring plunger 114, the plate 38 is resistibly pushed in the direction of arrow F about the pin 46 away from the carrier 18. The plate 38 thus pushes the entire drive train 34 away from the carrier 18 in the direction of arrow F. As the drive pulley 90 (FIG. 6) is pulled further away from the carrier 18, the belt 42 is tightened or tensioned about the C-arm 22 (FIG. 1), the idler wheels 52, and the drive pulley 90. By tensioning the belt 42 in this manner, the belt 42 is less likely to become slack or disengaged from the drive pulley 90. Therefore, the C-arm 22 will be more effectively rotated about the carrier 18 in the directions of arrows A and B.

The operator may alter the tension in the belt 42 about the C-arm 22 (FIG. 1) to a desired tension level by adjusting the screw 134 as necessary. For example, the further an operator screws the screw 134 into the plate 38, the greater the tension in the belt 42. Alternatively, should the operator wish to reduce the tension in the belt 42 about the C-arm 22 for maintenance or inspection purposes, the operator may screw the screw 134 out of the plate 38 away from the cap 120 such that the plate 38 then is allowed to move closer to the carrier 18.

The tension system disclosed herein may include alternative embodiments. For example, the tension system is not limited to use with medical imaging C-arms 22. Alternatively, the tension system may be used to control the tension in any other belt-driven machines where the belt 42 engages a curved arm. Alternatively, the drive train 34 may be configured to pivot and engage the spring plunger 114 without the use of the plate 38. Alternatively, any number of different engagement pieces besides a screw 134 may be used to engage the spring plunger 114. For example, the plate 38 may carry a bolt or pin that can be locked into the plate 38 at different depths such that the bolt or pin engages the spring plunger 114. Alternatively, the drive train 34 and tensioning system may be located at other points along the carrier 18 besides at a midway point. Alternatively, the tension system may include a spring 126 that engages the carrier 18 and the engagement piece without the use of a plunger that extends into the spring block 110. Alternatively, the tension system may not include a spring 126 at all, but may include a resistant, flexible member that engages the screw 134 or engagement piece. Alternatively, the spring plunger 114 may not include the cap 120, but rather the screw 134 may be configured to engage the spring 126 directly.

The tensioning system of the embodiments provides several advantages over the prior art. First, by engaging the screw 134 with the spring loaded plunger 114, the plate 38 is not rigidly held in place between the pull of the belt 42 and the push of the spring plunger 114. Therefore, the plate 38 may still be moved far enough away from the carrier 18 to adequately increase the tension in the belt 42 while at the same time being able to move slightly back to the carrier 18 against the spring 126 to accommodate any tightening of the belt 42 as the belt 42 moves.

Additionally, as the belt 42 wears and becomes looser about the C-arm 22 and the idler wheels 52 due to use, the screw 134 does not necessarily have to be tightened further to increase the tension in the belt 42. The spring plunger 114 will be under less compression from the screw 134 and plate 38 because the belt 42 is placing less pressure on the plate 38, and thus the spring 126 can expand and push the plate 38 further from the carrier 18. Thus, the interaction of the screw 134 and spring 126 continuously operate together to push the plate 38 further away from the carrier 18 in order to tighten the belt 42 as the belt 42 slackens after repeated use.

Also, by placing the tensioning system midway along the carrier 18 and thus midway along the C-arm 22, the tensioning system is able to tension the belt 42 on both sides of the drive pulley 90 regardless of the direction the C-arm 22 is being rotated. Thus, the belt 42 is generally equally well tensioned at both distal ends 25 and 27 of the C-arm 22. Furthermore, the tensioning system of the different embodiments is easy to use because the operator simply rotates the screw 134 to loosen or tighten the belt 42 about the C-arm 22. Additionally, the tensioning system of the different embodiments takes up very little space. Instead of being positioned on either or both distal ends 25 and 27 of the C-arm 22, the system is entirely localized behind the carrier 18 and thus out of the way of the patient, operator, or any other objects in the room. The tensioning system also saves space by positioning the drive train 34 on the carrier 18 instead of connecting a separate stationary drive train 34 to the carrier 18. Thus, the drive train 34 is out of the way of the operator and moves with the carrier 18 so as not to limit or constrain the movement of the carrier 18. Also, the tensioning system combines a drive train 34 with a mobile C-arm imaging machine 10, which greatly increases the versatility and operator control of the C-arm imaging machine 10.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A system for controlling an imaging device having a curved imaging arm comprising:
   a carrier that engages and supports the curved imaging arm such that the curved imaging arm can be moved along said carrier;
   a belt extending through said carrier and secured to the curved imaging arm;
   a drive system for receiving and driving said belt to move the curved imaging arm relative to said carrier; and
   a tensioning mechanism, wherein said drive system and said tensioning system are mounted on a plate configured to move relative to said carrier, said tensioning mechanism extending from said plate to engage said carrier from said plate to move said plate in such a direction relative to said carrier in order to increase the tension on said belt and to move in such a direction relative to said carrier in order to decrease the tension on said belt.

2. The drive system of claim 1, wherein said carrier includes a spring mechanism and said tensioning mechanism includes an engagement piece that engages said spring mechanism such that said tensioning mechanism is pivoted relative to said carrier to increase the tension in said belt.

3. The drive system of claim 1, wherein said plate carries a screw and said carrier includes a spring mechanism, said screw threadably screwing through said plate to engage said spring mechanism to move said plate relative to said carrier.

4. The drive system of claim 1, wherein the curved arm is a medical imaging C-arm that carries an imaging source and an imaging receiver to image areas of interest on a patient's body.

5. The drive system of claim 1, wherein said carrier includes a spring positioned about a plunger having a cap, said plunger extending into said carrier upon contact with said tensioning mechanism such that said spring is compressed between said cap and said carrier in order that said tensioning mechanism is pushed away from said carrier.

6. The drive system of claim 1, wherein said carrier includes a foot having a pin, said plate having a hole extending therethrough, said hole receiving said pin such that said plate rotates about said pin relative to said foot and said carrier.

7. The drive system of claim 1, wherein said drive system is mounted on said plate on a side of the plate opposite said carrier, said plate having a hole through which said belt extends from said drive system to said carrier.

8. The drive system of claim 1, wherein the curved arm has opposite distal ends and said drive system is positioned between said opposite distal ends.

9. A drive system, comprising:
   a mobile curved imaging arm;
   a carrier that engages and supports said curved imaging arm, said carrier including a spring mechanism connected thereto;
   a belt extending through said carrier and secured to said imaging curved arm; and
   a driving system configured to pivot about said carrier, said driving system receiving and driving said belt such that said curved imaging arm moves relative to said carrier, said driving system including an engagement piece such that said engagement piece extending from said driving system engages said spring mechanism, said spring mechanism resisting said engagement piece such that said driving system is pivoted in such a direction relative to said carrier that said driving system is pulled away from said curved imaging arm and said belt increases in tension about said curved imaging arm.

10. The drive system of claim 9, further including a plate upon which said driving system is mounted, said plate pivoting about said carrier.

11. The drive system of claim 9, wherein said driving system is mounted on a plate and said engagement piece extends through said plate to said spring mechanism.

12. The drive system of claim 9, wherein said driving system is mounted on a plate and said engagement piece is a screw that threadably screws through said plate to engage said spring mechanism.

13. The drive system of claim 9, wherein said spring mechanism includes a spring positioned about a plunger having a cap, said plunger extending into said carrier upon contact with said engagement piece such that said spring is compressed between said cap and said carrier in order that said engagement piece is pushed away from said carrier.

14. The drive system of claim 9, wherein said carrier includes a spring block that carries said spring mechanism and receives a portion of said spring mechanism as said engagement piece engages said spring mechanism.

15. The drive system of claim 9, wherein said driving system is mounted on a plate and said carrier includes a foot having a pin, said plate having a hole extending therethrough, said hole receiving said pin such that said plate rotates about said pin relative to said foot and said carrier.

16. The drive system of claim 9, wherein said curved arm has opposite distal ends and said driving system is positioned between said opposite distal ends.

17. The drive system of claim 9, wherein said curved arm has opposite distal ends and said belt is connected to said curved arm at said distal ends.

18. The drive system of claim 9, wherein said driving system is mounted on a plate on a side of the plate opposite said carrier, said plate having a hole through which said belt extends from said driving system to said carrier.

19. The drive system of claim 9, wherein said curved arm is a medical imaging C-arm that carries an imaging source and an imaging receiver to image areas of interest on a patient's body.

20. A system for controlling an imaging device having a curved imaging arm, comprising:

a mobile curved imaging arm;

a carrier that supports said curved imaging arm, said carrier including a spring mechanism connected thereto;

a belt extending through said carrier and secured about said curved imaging arm; and a driving system mounted to a plate configured to move relative to said carrier, said driving system receiving and driving said belt such that said curved imaging arm moves relative to said carrier, said plate including an adjustable engagement piece that engages said spring mechanism of said carrier such that said driving system is moved in such a direction relative to said carrier that said belt increases or decreases in tension about said curved imaging arm.

* * * * *